July 6, 1965 F. W. ANDERSON Plant Pat. 2,543
APRICOT TREE
Filed Feb. 24, 1964
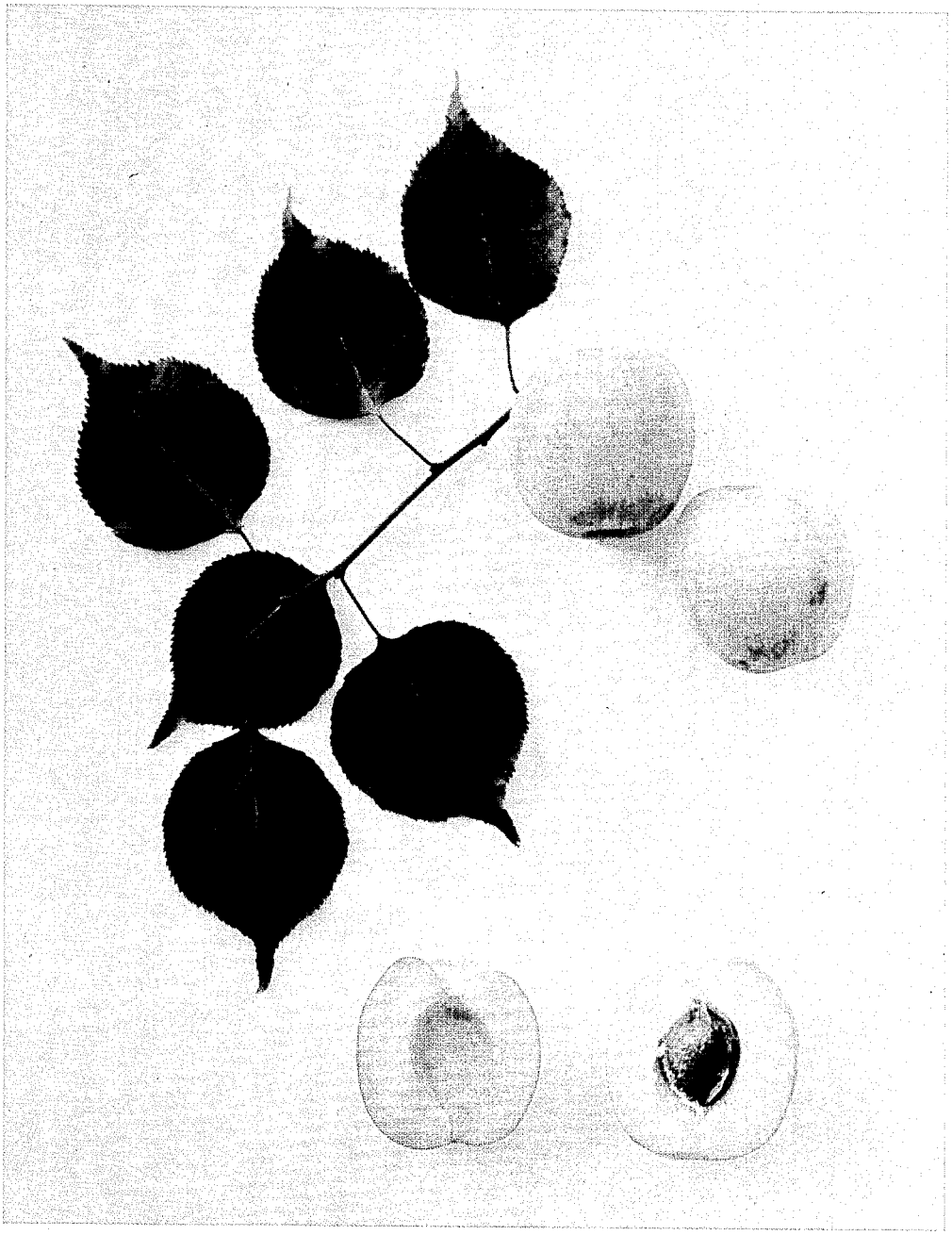
INVENTOR
*Frederic W. Anderson*
*Webster & Webster*
ATTYS.

United States Patent Office

Plant Pat. 2,543
Patented July 6, 1965

2,543
APRICOT TREE

Frederic W. Anderson, Merced, Calif., assignor to Irvin M. Burchell, doing business as The Burchell Nursery, Modesto, Calif.

Filed Feb. 24, 1964, Ser. No. 347,104
1 Claim. (Cl. Plt.—39)

This invention relates to a new and distinct variety of apricot tree which bears medium to large size fruit of good quality and well adapted for dessert and canning use.

The present variety of apricot tree was originated by me in my experimental orchard located near Le Grand, Merced County, California, during the course of a long and continuing program seeking improved fruit varieties, including apricots.

More particularly, the variety is a second generation seedling of the Perfection (unpatented). Seeds of the self-sterile Perfection were obtained from trees closely adjoining trees of the two leading apricot varieties; viz. the Blenheim and Tilton (both unpatented). A large number of first generation seedlings, resulting from the planting of such seeds, were grown to maturity. From such of these first generation seedlings that evidenced desirable characteristics, seeds were obtained and planted, and from the resulting second generation seedlings the present variety was selected as being distinctive and having commercially desirable features as hereinafter described.

Subsequent to origination of the variety, as above, I asexually reproduced it by top-working on mature trees in my experimental orchard located as aforesaid. In maturity, all of such asexual reproductions ran true to the parent tree in all respects.

As one advantageous feature, the fruit of the present variety ripens about ten days before the Blenheim and the harvest is completed before the latter is started in harvest. Thus, the present variety will permit the apricot canning season to begin approximately a week earlier than at present.

Of further advantage, and again in comparison with the Blenheim, the fruit of the present variety averages somewhat larger in size, ripens more evenly, and has firmer flesh; the latter having a soluble solid content varying from twenty to twenty-five percent by saccharometer test.

Of still further advantage, the fruit of the present variety apparently is not subject to the defect known as "heat burn"; i.e. the turning of the flesh to a black color under conditions of relatively high pre-harvest daytime temperature. In comparison, the Blenheim is subject to such defect and thus is not especially satisfactory when grown in an area where the daytime temperature sometimes exceeds 100 degrees F.

The drawing is an illustration, by photographic reproduction in color, of a twig with leaves and fruit at the time of harvest; one fruit being shown as cut in half to expose the flesh and with the stone remaining in one half.

Referring now more specifically to the pomological details of this new and distinct variety of apricot tree, the following is an outline description thereof; all major color plate identifications being by reference to Maerz and Paul Dictionary of Color, in comparison with fresh specimens.

Tree:
- *Size.*—Medium.
- *Vigor.*—Medium.
- *Growth.*—Spreading.
- *Density.*—Open.
- *Production.*—Productive.
- *Bearing.*—Regular bearer.

Trunk:
- *Form.*—Medium.
- *Texture.*—Medium.

Branches: Form—Medium. Texture—medium.
- *Lenticels.*—Number—medium. Size—large.

Leaves:
- *Size.*—Large. Average length—3¼". Average width—2⅝".
- *Form.*—Cordate; acutely pointed.
- *Thickness.*—Medium.
- *Texture.*—Smooth.
- *Margin.*—Coarsely serrate.
- *Petiole.*—Medium length: medium thickness.
- *Glands.*—Average number and position—3 to 5 on petiole and 2 on blade. Alternate; small; globose.
- *Color.*—Top side—medium green (22–I–8); under side—lighter green (21–G–8).

Flower buds:
- *Size.*—Medium to small.
- *Length.*—Short.
- *Form.*—Conic.

Flowers:
- *Date of first bloom.*—February 25, 1963.
- *Date of full bloom.*—March 5, 1963; early, about 3 days before Blenheim.
- *Size.*—Medium.
- *Color.*—Pinkish before flowers open; almost completely white at full bloom.

Fruit:
- *Maturity when described.*—Eating ripe—June 24, 1963.
- *Dates of first and last picking.*—June 14, 1963, and June 24, 1963, respectively.
- *Size.*—Uniform; medium to large; average diameter axially—2"; average transversely in suture plane—2".
- *Form.*—Uniform; symmetrical; globose; compressed laterally; occasional fruit have unequal halves and a somewhat pebbly surface.
- *Suture.*—Distinct but shallow; extends from base to apex.
- *Ventral surface.*—Rounded strongly.
- *Cavity.*—Average depth—⅜"; average breadth—⅝".
- *Base.*—Rounded.
- *Apex.*—Short; depressed.

Skin:
- *Thickness.*—Medium.
- *Texture.*—Medium.
- *Tenacity.*—Tenacious to flesh.
- *Tendency to crack.*—Slight.
- *Down.*—Scant; short.
- *Color.*—Normal apricot (10–L–8).

Flesh:
- *Juice.*—Moderate.
- *Texture.*—Firm; meaty.
- *Fibers.*—Few.
- *Ripens.*—Evenly.
- *Flavor.*—Subacid; delicate; soluble acids vary from 20 to 25 degrees on a fruit saccharometer; titratable acidity unknown.
- *Eating quality.*—Good to best.
- *Color.*—Normal apricot (9–L–7).

Stone:
- *Type.*—Free.
- *Fibers.*—Short.
- *Size.*—Medium; average length—1"; average breadth—¾"; average thickness—9/16".
- *Form.*—Oval.
- *Base.*—Straight.
- *Apex.*—Rounded.
- *Sides.*—Equal.
- *Ventral edge.*—Thick.

*Dorsal edge.*—Narrow, with shallow groove toward base and apex.

*Tendency to split.*—Very slight.

*Color.*—Brown (8–E–12).

Use: dessert, shipping, drying, freezing, canning.

Keeping quality: Good.

Shipping quality: Good.

The apricot tree and its fruit herein described may vary in slight detail due to climatic and soil conditions under which the variety may be grown; the present description being of the variety as grown in the Central Valley of California.

The following is claimed:

A new and distinct variety of apricot tree, substantially as illustrated and described, which is a regular and productive bearer of medium to large size fruit of good quality; characterized, in comparison with the Blenheim, by fruit which ripens more evenly and about ten days earlier, averages larger in size, and has firmer flesh.

No references cited.

ABRAHAM G. STONE, *Primary Examiner.*